United States Patent [19]
Yoshida

[11] 3,985,028
[45] Oct. 12, 1976

[54] SAMPLE COLLECTING APPARATUS
[75] Inventor: Takeshi Yoshida, Musashino, Japan
[73] Assignee: Kabushiki Kaisha Hokushin Denki Seisakusho, Tokyo, Japan
[22] Filed: Mar. 31, 1975
[21] Appl. No.: 563,369

[30] Foreign Application Priority Data
Mar. 29, 1974  Japan.............................. 49-36211
Oct. 9, 1974   Japan....................... 49-122759[U]

[52] U.S. Cl. ............................... 73/198; 73/421 B
[51] Int. Cl.² .......................................... G01N 1/14
[58] Field of Search......... 73/421 B, 422 R, 422 TC

[56] References Cited
UNITED STATES PATENTS
2,637,211  5/1953   Norman ............................ 73/422 R
2,925,735  2/1960   Tapp et al. ..................... 73/422 TC
2,927,465  3/1960   Smith .............................. 73/422 R Primary Examiner—S. Clement Swisher
Attorney, Agent, or Firm—Walter Becker

[57] ABSTRACT

An apparatus for continuously collecting small-amount samples from a stream in response to the flow rate of the stream. The apparatus includes piston cylinder means which can receive a sample of the volume proportional to the measured flow rate and subsequently discharge the collected sample into sample collecting or storing means. The piston cylinder means comprises a piston member and a cylinder member. During the sample collecting cycle, the piston member moves by a distance corresponding to the measured flow rate during a constant period of time. This piston moving distance defines the amount of the sample to be collected. During the subsequent sample discharging operation, the piston is quickly returned and the collected sample is discharged. These cycles are automatically repeated.

11 Claims, 3 Drawing Figures

SAMPLE COLLECTING APPARATUS

BACKGROUND OF THE INVENTION

This invention relates generally to a sample collecting system and, more particularly to a sampling apparatus for successively collecting small-volume samples from a fluid stream of factory waste water for example, the flow rate of which varies with time, the volume of the respective collected sample being proportional to the flow rate of the stream during the sample collecting cycle.

Recently the problems relating to public pollution has become so serious that, even with respect to the "control of water quality" of waste water from factories etc., the "control of total amount" is on the verge of being put into practice in place of the conventional "control of concentration". In the case of the control of total amount, it is needed to integrate or continuously add the products of the amount and concentration of waste water during the whole measurement period of time so as thereby to determine the total amount of pollution substance for the given period of time. It would be possible to known the total amount of the pollution substance by continuously measuring and multiplying the amount and concentration of the waste water to provide the integrated value, but in such a case, the apparatus therefor becomes very complicated and expensive.

In order to overcome such disadvantage, a sampling system has been proposed wherein from waste water which is to be subjected to the control of total amount, a small quantity of sample the volume of which is proportional to the flow rate of the waste water is picked up. Such liquid samples are accumulated without change of water quality during a predetermined period, and the amount of pollution substance included in the accumulated liquid sample is measured by using an analyzer, whereby the total amount of the pollution substance which was dashed together with the waste water is estimated. Since according to this system, it is not necessary to simultaneously measure the flow rate and concentration, the apparatus becomes simple, and the total amount of the pollution substance can be ascertained by a simple analyzer, and, accordingly, this system is very promising as a waste water measuring apparatus for small and medium enterprises which cannot afford a heavy equipment investment.

However, since such prior sampling apparatus was one wherein the samples are intermittently collected in proportion to the flow rate of the waste water stream, it could not perform a completely continuous measurement, and especially, in cases where a considerable variation in the quality of the samples exists, the system would possibly produce a great error.

SUMMARY OF THE INVENTION

One main object of this invention is to provide a sampling apparatus wherein small-amount samples can be successively collected from the stream of waste water in proportion to the flow rate of the stream and therefore an entirely continuous measurement of the total amount of pollution substance in waste water can be obtained.

In accordance with this invention, there are provided means for measuring the flow rate of the stream to provide an output signal representative thereof. Preferably, this measuring means emits a pulse signal the pulse rate of which is proportional to the flow rate of the stream. There are also provided sample collecting or storage means and means for receiving a sample from the stream and subsequently discharging the received sample into the sample storage means. This sample receiving means is selectively connected to the stream or to the sample storage means. Preferably, the sample receiving means comprises piston cylinder means. This piston cylinder means comprises at least one piston cylinder. When the piston cylinder is connected to the stream, a sample collecting cycle is commenced wherein the piston cylinder receives from the stream a sample the volume of which is proportional to the flow rate of the stream during the sample collecting cycle. The sample collecting cycle is set for a constant period of time. When the piston cylinder is connected to the sample storage means, a sample discharging cycle is commenced wherein during a short time the collected sample is discharged to the sample discharging means. If a pair of piston cylinders are used, the piston cylinders are alternately operated so that when one of them is in the sample collecting cycle, the other is in the sample discharging cycle, and, therefore, a more continuous measurement is obtainable without any interruption of the sample collecting operation. The sampling apparatus of this invention also comprises means responsive to the output signal from the measuring means for causing the sample receiving means to receive a sample of the volume related to the output signal. This means comprises piston reciprocating means. Preferably, the piston reciprocating means includes a pulse motor. When the sample collecting cycle is set, the pulse motor drives the piston during this cycle at a rate related to the output signal from the measuring means. The piston moving distance which relates to the output signal from the measuring means defines the volume of a sample to be collected within the piston cylinder means during the sample collecting cycle. Upon completion of the sample collecting cycle, the piston is quickly returned to its original position from which the piston will be driven again in a next sample collecting cycle. As the piston is returned, the collected sample within the piston cylinder means is discharged into the sample reserving means. Preferably, the cylinder has a tapered bottom portion with the lowest end connected to the sample discharging line which is in turn connected to the sample reserving means. This lowest end may be selectively connected to the stream or the sample storage means in the respective cycle of operation. Also, means for providing a head difference with respect to the sample in the piston cylinder may be provided. This means includes fluid path means for increasing the level of the stream from which the samples are collected in comparison to the level of the piston cylinder means. With this arrangement, it becomes possible to use a mere simple water seal construction between the piston and cylinder of the piston cylinder means, in place of an expensive and complicated air seal construction. A bellow-phragm comprising a suitable flexible material such as rubber can be used as the water seal. Furthermore, in order to return the piston quickly to the original starting position to discharge the collected sample during the sample discharging cycle, one embodiment of this invention uses an electric motor, but the other embodiment uses the force of gravity, that is, the weight of the piston. Also, according to a preferred embodiment of this invention, a cleaning device is provided. This cleaning device comprises means for flushing an air jet in the sample receiving line which is adapted to be connected to the piston cylinder means. This air flushing means is actuated just before the sample receiving line is connected to the piston cylinder means, that is, the sample collecting cycle starts at or a short time after the sample receiving line is connected to the piston cylinder means.

BRIEF DESCRIPTION OF THE DRAWINGS

This invention will be more readily understood by reference to the following drawings, in which.

DESCRIPTION OF EMBODIMENTS

Figure 1:
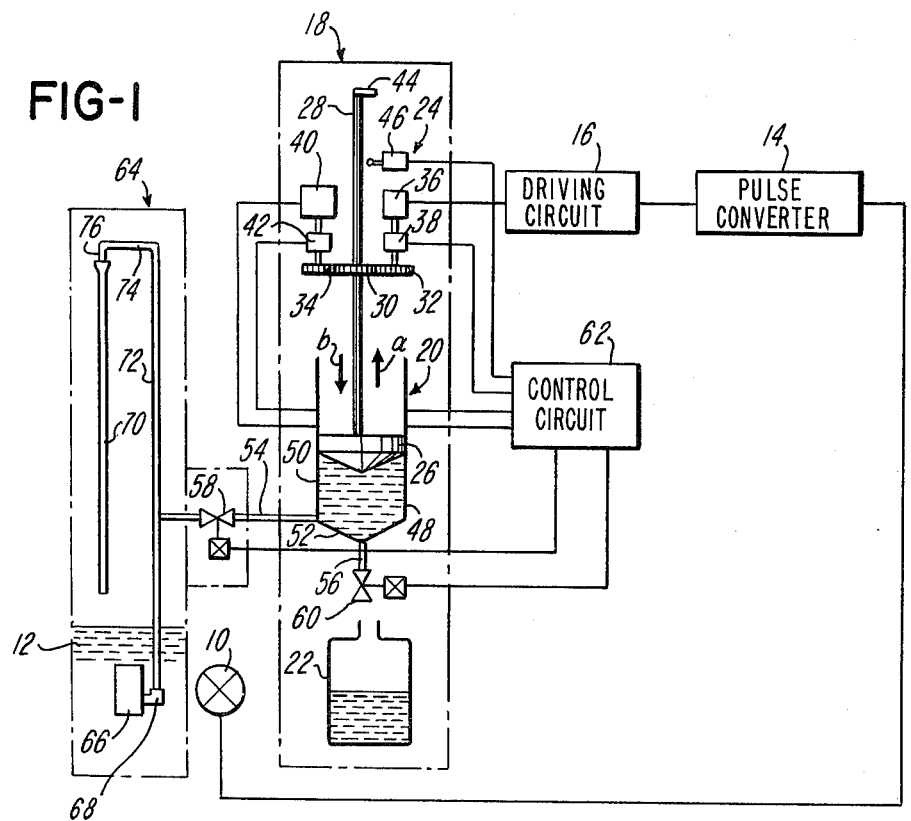
FIG. 1 is a diagrammatic representation of one embodiment of the invention.

A sampling apparatus according to this invention shown in FIG. 1 comprises a flow meter 10 for measuring the flow rate of the stream 12 of waste water, for example, from a factor. The flow meter 10 provides a continuous output signal in the form of an electric signal the level of which varies in proportion to the flow rate of the stream 12. This continuous signal is converted in a pulse converter into a pulse signal. The pulse rate or frequency of the pulse signal output from the pulse converter 14 varies with the level of the continuous signal from the flow meter 10 and hence with the flow rate of the stream 12. This pulse signal is supplied to a pulse motor driving circuit 16 which may be a conventional pulse power-amplifier.

The sampling apparatus further comprises a sample collecting and reserving device which is generally indicated in the drawing by reference numeral 18. The sample collecting and reserving device 18 includes a piston cylinder 20, a sample storage bottle 22 and a mechanism 24 for reciprocating the piston 26 of the piston cylinder 20. The mechanism 24 includes a gear shaft 28 which is connected to the piston 26 and moves in unison therewith. It should be noted from FIG. 1 that the moving direction of the piston 26 corresponds to the axis of the gear shaft 28. The piston reciprocating mechanism 24 further includes a gear 30 and a pair of other gears 32 and 34. The gear 30 is rotatably supported by a suitable support member which is in turn attached to the frame of the apparatus. The gear 30 has inner and outer threaded portions. The inner threaded portion thereof is engaged with the gear shaft 28 so that the rotation of the former is converted into the axial and linear movement of the latter, and the outer threaded portion of the gear 30 is drivingly engaged to the gears 32 and 34. The gear 32 is connected to a pulse motor 36 through a clutch 38 and the gear 34 is connected to a quick-return motor 40 through another clutch 42. The pulse motor 36 is energized by the above-mentioned driving circuit 16 and drives the gear shaft 28 in a step-by-step manner in the direction $a$. The motor 40 drives the gear shaft 28 continuously and quickly in the direction $b$. The gear shaft 28 is provided with a hooked portion 44 at its free end. The hooked portion 44 is adapted to engage a micro-switch 46 when the piston 26 drops to its maximum lower position.

The piston cylinder 20 has a cylinder member 48 within which the piston member 26 moves. The cylinder 48 is formed by a cylindrical portion 50 and a tapered lower portion 52 the shape of which substantially corresponds to the lower end portion of the piston 26. The cylinder 48 has a sample receiving conduit line 54 and a sample discharging conduit line 56. Suitable gating members 58 and 60 such as electro-magnetic valves, are provided in the lines 54 and 56, respectively.

A control circuit 62 is connected to the clutches 38 and 42, the micro-switch 46, the quick-return motor 40 and the valves 58 and 60 and controls the operation of the apparatus which will be stated in detail hereinafter.

The sampling apparatus includes a pumping device which is generally identified by reference numeral 64. The pumping device 64 comprises an under-water pump 66 which is positioned in the stream 12, a liquid rising pipe 68 connected to the pipe 66 and a liquid returning pipe 70. The liquid rising pipe 68 has an elongated vertical portion 72 and an upper horizontal portion 74 and a vertical free-end portion 76. Liquid from the free end portion 76 is received by the liquid returning pipe 72. The sample receiving conduit 54 is connected to the elongated pipe portion 72 at the lower position of the latter. It is noted that the horizontal pipe portion 74 is positioned at a higher level than that of the piston cylinder 20. Therefore, this pumping arrangement provides a suitable head difference between the pressure of the liquid passing through the pipe 68 and that of the liquid in the piston cylinder.

In operation, firstly, it is assumed that the piston 26 is in the maximum lower position wherein preferably there is no liquid within the cylinder 48, the clutch 38 is engaged, the clutch 42 is disengaged, the valve 58 is opened and the valve 60 is closed. In these initial conditions, when a flow-rate signal is emitted from the flow meter 10, this signal is converted in the pulse converter 14 into the pulses of the frequency which is proportional to the flow rate, and these pulses are applied to the driving circuit 16 to rotate the pulse motor 36. When the pulse motor 36 rotates, the piston 26 ascends together with the gear shaft 28 in the direction $a$. Since there is the head difference between the piston cylinder 20 and the pumping line 64, by merely forming the seal between the piston 26 and the cylinder 48 as a suitable water-sealing construction in place of using an entirely air-sealing construction, it is possible to introduce liquid into the piston cylinder 20, and, therefore, it is obtainable to lift the piston 26 in the direction $a$ by a relatively small driving force. As a result, a liquid sample is received by the piston cylinder 20 through the pipe 68 and the sample introducing conduit 54 with the opened electro-magnetic valve 58. Since the rising speed of the piston 26 is proportional to the speed of rotation of the pulse motor 36, that is, to the flow rate of the stream 12, it follows that the quantity of flow of a sample which is introduced into the cylinder is proportional to the flow rate of the main stream 12.

After a predetermined period of time has elapsed, the control circuit 62 applies commands to the quick-return motor 40, the clutches 38 and 42 and the valve 58 and 60. Whereupon the motor 40 rotates, the clutch 42 engages and the clutch 38 disengages and the valve 58 closes and the valve 60 opens. The motor 40 drives the piston 26 in the direction $b$ to the original maximum lower position at a quick speed. Therefore, the sample which has been collected within the cylinder during the sample collecting cycle or mode is discharged through the sample discharging conduit 56 into the sample collecting bottle 22 which is preferably maintained in a cooling space so as to avoid any change in quality of the reserved sample. Thereafter, the samples in the bottle 22 will be analyzed to determine the amount of the pollution components.

When the piston 26 returns to its maximum lower position, the limit-switch is actuated to provide a signal to the control circuit 62 so that the latter controls the clutches 38 and 42 and the valves 58 and 60 to establish the above-mentioned initial conditions wherein the clutch 38 engages and the clutch 42 disengages, and the valve 58 opens and the valve 60 closes. At the same time, the sampling cycle starts. These sample collecting and discharging cycles are automatically repeated.

From the above description, it should be understood that the period of time for the sample collecting cycles is the same which has been preset by the control circuit 62, but the amount of the collected sample in the cylinder is variable depending upon a maximum raising position of the piston 26 in a sample collecting cycle, that is, upon the flow rate of the stream 12 in that sample collecting cycle.

Figure 2:
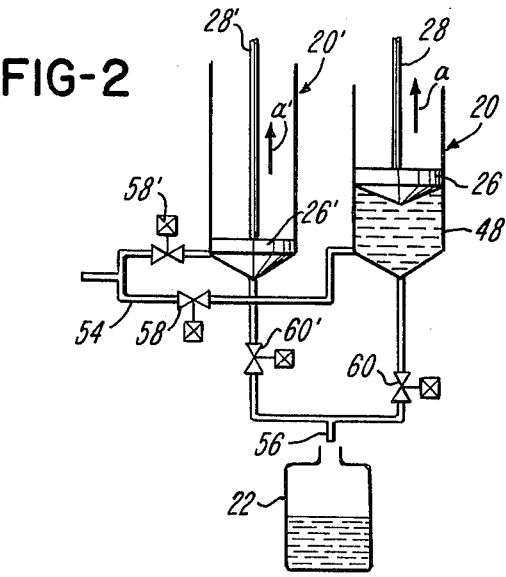
FIG. 2 is a modification of a portion in FIG. 1.

FIG. 2 shows a modification of the embodiment shown in FIG. 1 wherein the same elements as used in FIG. 1 have the similar reference numerals. The arrangement in FIG. 2 includes a pair of piston cylinders 20 and 20' which are alternately driven so that when one of them is operated in a simple collecting cycle the other is in the sample discharging cycle. At this end, the period of time for the sample collecting cycle and that for the sample discharging cycle are set the same. FIG. 2 shows a condition at the time when the piston cylinder 20 has just completed the sample collecting cycle and the piston cylinder 20' additionally provided has just completed the sample discharging cycle. With this arrangement, the interruption of the sample collecting operation can be avoided which exists in case when a single piston cylinder is used and when it is in the sample discharging cycle, and an entirely continuous measurement can be attained.

Other modifications can be made to the apparatus shown in FIG. 1. For example, a servo-motor with a tach-generator for speed feedback, in place of the pulse motor 36 for driving the piston 26 during the sample collecting mode. Further, in the illustrated embodiment, the quick-return motor 40 is additionally provided, but it is possible to use the pulse motor 36 to provide this quick-return operation as well as the sample collecting mode operation. Furthermore, a pair of electro-magnetic valves 58 and 60 are used as the connection switching means of the liquid flowing paths for collecting and discharging the sample respectively, but this invention should not be limited to this. For example, a mechanism may be used wherein the cylinder chamber which is adapted to be defined by the piston 26 and the cylinder 48 is connected to either the pumping device 64 or the sample reserving bottle 22 by a command signal from the control circuit 62. Also, if the piston 26 is lowered at the speed proportional to the input signal, contrary to the case of the embodiment shown, then the piston cylinder can be used as a control pump for continuously discharging the liquid of the volume proportional to the input signal. Also, this invention has been explained as one wherein the moving speed of the piston 26 in the sample collecting cycle is controlled by the signal proportional to the flow rate of the main stream, but this invention also includes such a system that the flow rate signals are once integrated to provide an integrated signal which controls the position (a maximum raising position in a sample collecting cycle) of the piston 26.

Figure 3:
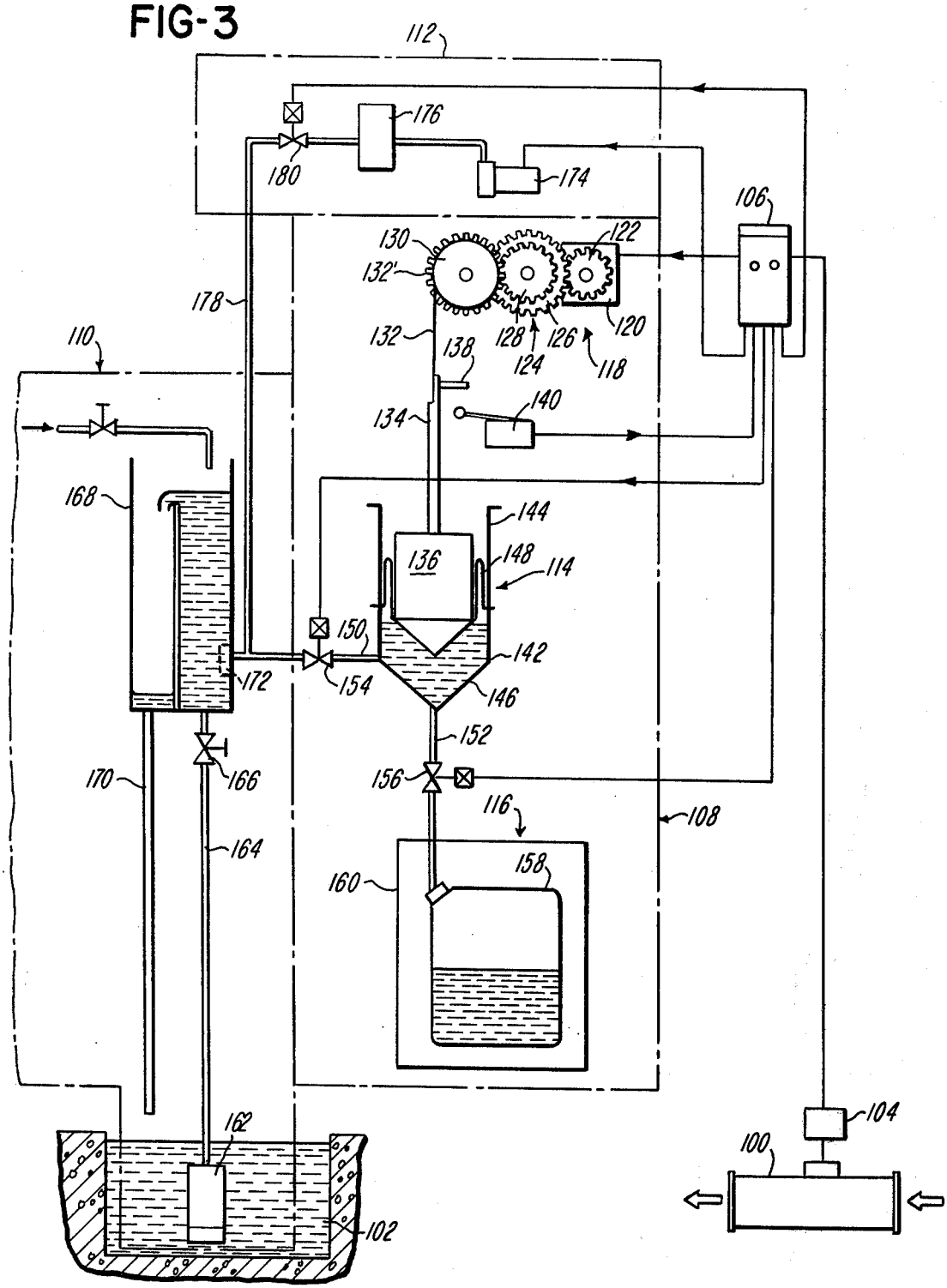
FIG. 3 is a diagrammatic representation of a second embodiment of the invention.

FIG. 3 shows another embodiment of this invention comprising a flow meter 100 for sensing the flow rate of the stream 102, a pulse converter 104 and a pulse motor driving circuit 106. The flow meter 100 corresponds to the flow meter 10 in FIG. 1. The pulse converter corresponds to the pulse converter 104 in FIG. 1. The pulse motor driving circuit 106 corresponds to the pulse motor driving circuit 16, but the former further includes a control circuit for controlling the operation of the apparatus. The sampling apparatus shown in FIG. 3 further comprises a sample collecting and storing device which is generally indicated by reference numeral 108, a liquid pumping device which is generally indicated by reference numeral 110, and a cleaning device which is generally indicated by reference numeral 112.

The sample collecting and storing device 108 includes a piston cylinder 114, a sample storing device 116 and a piston reciprocating mechanism 118. The mechanism 118 has a pulse motor 120 driven by the current pulses from the circuit 106. The pulse motor 120 has its rotating shaft with a gear 122 which is drivingly engaged with a large gear 126 of a clutch 124. The clutch 124 has a small gear 128 which meshes with a gear 132 of pulley 130 around which a belt 132 is wound. One end of the belt 132 is coupled to the rod 134 of the piston 136 of the piston cylinder 114. The piston rod 134 is provided with a pin 138 adjacent the free end of the piston rod 134. The pin 138 triggers a micro-switch 140 when the piston 136 reaches its maximum lower position in the sample discharging cycle. When the micro-switch 140 is triggered, a signal is applied to the circuit 106 for starting the sample collecting cycle.

The piston cylinder 114 has a cylinder 142 comprising a cylindrical portion 144 and a tapered portion 146. A bellow-phragm 148 comprising a suitable flexible diaphragm such as rubber, etc. is provided between the cylindrical side of the piston 136 and the cylindrical portion 144 of the cylinder 142. The cylinder 142 is connected to the pumping device 110 by a sample receiving conduit line 150 corresponding to the line 54 in FIG. 1 and to the sample reserving device 116 by a sample discharging conduit line 153 corresponding to the line 56 in FIG. 1. The lines 150 and 152 include electromagnetic valves 154 and 156, respectively, which are controlled by the circuit 106 and correspond to the valve 58 and 60 in FIG. 1 respectively.

The sample storage device 116 includes a sample storage vessel 158 and a cooling box 160. The sample discharged from the cylinder 142 is received by a vessel 158 through the sample discharging conduit line 152.

The pumping device 110 includes an under water pump 162, a liquid raising pipe 164, with a manual operated valve 166, a tank 168 and a liquid return pipe 170. The tank 168 always receives liquid from the pump 162. It should be noted that the level of the pumped liquid in the tank 168 is at all times higher than that of the sample in the cylinder. Overflowed liquid in the tank 168 is returned to the main stream 102 through the pipe 170. A filter 172 is arranged in the tank 168, through which a sample in introduced in the sample receiving conduit 150.

The level of the pumped liquid in the tank 168 is so set that in the sample collecting cycle the pressure of the liquid sample in the piston cylinder 114 is greater than that of atmospheric air. Therefore, the bellow-phragm type water seal can be used which offers the least friction against dropping due to the force of gravity of the piston 136 in the sample discharging cycle.

Especially, in accordance with this embodiment, the cleaning device 112 is provided with an air compressor 174. The compressed air from the compressor 174 is stored in an air tank 176. This tank is coupled to the sample receiving conduit line 150 at its position adjacent to the tank 168, through a pipe 178 including an electromagnetically operated flush valve 180. The valve 180 is opened just before the piston 136 reaches its maximum lower position whereupon the limit switch 140 is actuated and the valve 154 is opened thereby, or during a short time after the valve is opened. While the valve 180 is opening, air jet is flushed into the sample receiving conduct line 150 to make the inside thereof clean and remove dust attached to the filter 172. The air jet also acts to prevent liquid from being introduced into the piston cylinder 114 at that time. This air pressure is sufficient to be on the order of 0.5 kg/cm².

The clutch 124, the valves 154, 156 and 180 and the air compressor 174 are controlled by the controller 106. In the initial condition of the sample collecting cycle, the clutch 124 is engaged, the valve 154 is opened and the valve 156 is closed. The piston 136 is moved upward in proportion to the flow rate of the main stream 102 for 15 minutes, for example. Therefore, a sample of the volume proportional to that flow rate is introduced into the piston cylinder 114. When the sample discharging cycle is commenced just after the piston 136 has been raised for the 15 minutes, the valve 154 is closed, the valve 156 is opened and the clutch 124 is disengaged, so that the piston 136 is quickly lowered by its weight. At that time, the liquid sample contained in the piston cylinder 114 is discharged into the vessel 158. When the piston 136 reaches its maximum lower position, the sample discharging cycle is completed. In response to the completion of the sample discharging cycle, the valve 154 is opened and the flush valve 180 is opened for about two seconds to rinse the sample receiving conduit 150 and the filter 172. Three minutes before the flush valve 180 is opened, the air compressor 174 is actuated to store compressed air within the air tank 176. While the flush valve is opened, the discharging valve may or may not be closed. The above-mentioned cycles are repeated automatically. The period for the interruption of the sample collecting operation becomes less than five minutes which is considerably short in comparison to the period for the sample collecting cycle which is 15 minutes.

According to the embodiment of FIG. 3, it is possible to successively collect the samples in proportion to the flow rate of the stream 102, and especially this exemplary apparatus is useful in cases where the change in quality of the sample is large. However, since the speed of liquid passing through the sample receiving conduit line 150 becomes very slow to the extent of several cc per minute, for example, there exists the possibility of depositing dust or the other material onto the inner wall of the conduit 150. Such deposit can be removed by the air jet, and the conduit line 150 is cyclically or periodically cleaned. At the same time, the cleaning of the filter 172 is also performed. This is effected by means of the single air pressure pipe 178. Further, since air is used for cleaning, there is no danger that the cleaning medium is mixed with the sample, unlike the case where water is used, and the cleaning can be carried out in a short time. The liquid which remains in the conduit 150 just prior to the cleaning is carried away into cylinder 142 or the vessel 158 by the jet and during the cleaning, the introduction of liquid through the filter 172 into the conduit line 150 is prevented by the air pressure, so that no excess liquid is collected. From the above point of view, the pipe 178 is connected to the line 150 at the nearer point to the end of the line 150 which connects to the tank 168, as much as possible.

In the illustrated embodiment, the bellow-phragm 148 has been used as a water seal between the piston 136 and the cylinder 142, but an O-ring can be also used in place thereof. Further, in the embodiment, in order to return the piston 136 to its original position, the pulley and belt assembly (130, 132) has been used, but an electric motor can otherwise be used. Also, the modification as shown in FIG. 2 is applicable to this embodiment. The other cleaning medium rather than air may be used.

It is, of course, to be understood that the present invention is, by no means, limited to the specific showing in the drawings but also comprises any modifications within the scope of the appended claims.

What is claimed is:

1. An apparatus for successively collecting small-volume samples from a fluid stream in response to the flow rate thereof, which includes: sample storing means, means for receiving a fluid sample from said stream and for subsequently discharging the received sample into said sample storing means, means for measuring the flow rate of said stream to provide an output signal representative thereof, means responsive to said output signal for causing said sample receiving means to receive a fluid sample of the volume related to said signal, said output signal being in the form of a pulse signal the pulse rate of which varies depending on the flow rate of said stream, said means responsive to said output signal including a pulse motor to which said pulse signal is applied during a predetermined period of time, and a mechanism drivingly connected to said pulse motor for driving said sample receiving means at a rate corresponding to said output signal to cause said sample receiving means to receive therein a sample of the corresponding volume, said sample receiving means including a piston cylinder with a piston member and a cylinder member, said members being adapted to define a sample receiving chamber, said piston being connected to said mechanism so that the former is driven by the latter during said predetermined period of time by a distance corresponding to the rate of said pulse motor.

2. An apparatus according to claim 1, wherein said sample receiving means comprises piston cylinder means with means for selectively and cyclically switching its sample receiving or discharging connection.

3. An apparatus according to claim 2, wherein said piston cylinder means comprises a pair of alternately operated piston cylinders.

4. An apparatus according to claim 2 wherein said piston cylinder means has a tapered bottom portion.

5. An apparatus according to claim 4, wherein the lowest end of said tapered bottom is connectable to a selected one of said sample receiving and discharging connections.

6. An apparatus according to claim 1, which includes means for providing a head difference with respect to the sample in said sample receiving means.

7. An apparatus according to claim 1, which includes means operable at the time of completion of said predetermined period of time to quickly return said piston to its starting position.

8. An apparatus according to claim 7, in which said piston quickly returning means comprises means using the weight of said piston.

9. An apparatus according to claim 1, which includes means for establishing a water seal between said piston and cylinder members.

10. An apparatus according to claim 9, in which said water sealing means comprises a bellow-phragm water seal.

11. An apparatus for successively collecting small-volume samples from a fluid stream in response to the flow rate thereof, which comprises in combination:
 a. sample storing means;
 b. means for receiving a fluid sample from said stream and for subsequently discharging the received sample into said sample storing means, said fluid sample receiving means including a piston cylinder with a piston member and a cylinder member, said both piston and cylinder members being adapted to define a sample receiving chamber;
 c. means for selectively and cyclically switching receiving and discharging connection into and out of said sample receiving means;
 d. means for measuring the flow rate of said stream to provide an output signal representative thereof; and
 e. means responsive to said output signal for causing said sample receiving means to receive a fluid sample of the volume related to said signal, said output signal responding means including:
  1. a pulse motor, to which said output signal in the form of a pulse signal with the pulse rate thereof varying in accordance with the flow rate of said fluid stream is applied during a predetermined period of time; and
  2. a mechanism which is drivingly connected to said pulse motor for driving said sample receiving means at a rate corresponding to said output signal to cause said sample receiving means to receive therein a sample of the corresponding volume, and to which said piston member is connected so as to be driven by said mechanism during said predetermined period of time by a distance corresponding to the rate of said pulse motor.

* * * * *

UNITED STATES PATENT OFFICE
CERTIFICATE OF CORRECTION

Patent No. 3,985,028  Dated October 12, 1976

Inventor(s) Takeshi Yoshida

It is certified that error appears in the above-identified patent and that said Letters Patent are hereby corrected as shown below:

On the title page item [75] "Musashino, Japan" should read -- Tokyo, Japan --.

Signed and Sealed this

Twenty-second Day of March 1977

[SEAL]

Attest:

RUTH C. MASON
Attesting Officer

C. MARSHALL DANN
Commissioner of Patents and Trademarks